(12) United States Patent
Harman et al.

(10) Patent No.: US 6,251,390 B1
(45) Date of Patent: Jun. 26, 2001

(54) PURIFIED CHITINASES AND USE THEREOF

(75) Inventors: Gary E. Harman; Roxanne M. Broadway, both of Geneva, NY (US); Arne Tronsmo, Aas (NO); Matteo Lorito; Christopher K. Hayes, both of Geneva, NY (US); Antonio Di Pietro, Binningen (CH)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 07/919,784

(22) Filed: Jul. 27, 1992

Related U.S. Application Data

(63) Continuation-in-part of application No. 07/716,134, filed on Jun. 17, 1991, now Pat. No. 5,173,419.

(51) Int. Cl.$^7$ .............................. A61K 38/47; C12N 9/42
(52) U.S. Cl. .................... 424/94.61; 435/209; 435/69.1; 514/12
(58) Field of Search .................................. 435/209, 69.1; 514/12; 424/94.61

(56) References Cited

U.S. PATENT DOCUMENTS

| | | | |
|---|---|---|---|
| 4,751,081 | 6/1988 | Suslow et al. | 424/93 |
| 4,940,840 | 7/1990 | Suslow et al. | 435/172.3 X |
| 5,290,687 | 3/1994 | Suslow et al. | 435/69.1 |

FOREIGN PATENT DOCUMENTS

| | | |
|---|---|---|
| 88/123645 | 11/1989 | (JP) . |
| 2-286082 | 11/1990 | (JP) . |

OTHER PUBLICATIONS

A. Arroyo–Begovich Meth. in Enzymology 161:471–474 1988.*
A. Ohtakara Meth. in Enzymology 161:463–470 1988.*
M. Pedraza–Reyes et al. Antonie Van Leeuwenhoek 59(3) 183–189 (1991).*
M. Pedraza–Reyes et al. Current Microbiology 22(1) 43–46 (1991).*
A. Ohtakara et al. "Isolation of Chitinase and Chitobiase Produced by *Pycnopones cinnabarinus* and their Properties" Chem. Absts. 95:348 (Aug. 1981).*
M. Yabuki "Chitinase and a Method for it's Production . . . " Derwent Biotechnol. Absts. 4(15)97 Abst Nos. 85–07729 & 85–07730 (Jul. 1985).*
A. Otakara "Studies on the Chitinolytic Enzymes of Black–koji Mold" Agric. Biol. Chem. 27(6) 454–460 (1963).*
G.W. Gooday "Physiology of Microbial Degradation of Chitin and Chitosan" Biodegradation 1(2–3) 177–190 (1990).*
Davies, D.A.L., et al, Nature, vol. 273, May 18, 1978, pp. 235–236
DeLa Cruz, J., et al, Eur. J. Biochem. 206, 859–867 (1992).
Klemsdal, S.S., et al, 11th Nordic Postgraduate School in Plant Pathology, abstract of poster presented Feb. 3, 1992 in Tisvildeleije, Denmark.
Tronsmo, A., Biological Control 1,59–62 (Aug. 1991).
Lorito, M., et al., Phytopathology, 82, No. 2, 245–246, (Feb. 1992).
Harman, G.E., et al, Proceedings of EFPP/IOBC Workshop, Copenhagen, Denmark, Jul. 1991.
De Vries, O.M.H., et al, J. Gen Microbiol., vol. 76, pp 319–330(1973).
Takara Biomedicals Brochure for Chitinase T–1, dated Apr. 1989, (Portion translated).
Takara Biomedicals Brochure for β–N–Acetylhexosaminidase from *Trichoderma harzianum* AF6–T8, dated Apr. 1989 (Portion translated).
Sivan, A., et al, J. Gen. Microbiol, vol. 135(3), pp. 675–682, Biosis Abstract.
Sandhu, D.K., et al, Enzyme Microb. Technol, Jan. 1989, vol. 11, pp. 21–25.
Usui, T., et al, Carbohydrate Research, 203, 65–77(1990).
Tronsmo, A., Aktuelt fra Statens Fagtjeneste for Landbruket 2, 107–113 (1985).
Tronsmo, A., Norwegian Journal of Agricultural Sciences 3:157–161 (1989).
Tronsmo, A., Phytopathology 79(10), 1153(1989).

* cited by examiner

*Primary Examiner*—Rebecca E. Prouty
(74) *Attorney, Agent, or Firm*—Nixon Peabody LLP

(57) ABSTRACT

Two chitinases from *Trichoderma harzianum* P1 (ATCC 74058) show chitin-containing-fungus-inhibiting activity. One is an endochitinase and the other is a chitobiase. Both have molecular weights of 40 kDa and isoelectric points of 3.9. A λgtll recombinant encoding for the endochitinase has been prepared (ATCC 55338) and the gene encoding for the endochitinase has been removed from the DNA of the recombinant by the restriction enzyme, Not I. Endochitinases and chitobiases including the two purified from *Trichoderma harzianum* strain P1 demonstrate synergy with each other in anti-fungal effect.

13 Claims, 8 Drawing Sheets

PURIFIED CHITINASES AND USE THEREOF

CROSS-REFERENCE TO RELATED APPLICATION

This is a continuation-in-part of U.S. Ser. No. 07/716,134, filed Jun. 17, 1991 now U.S. Pat. No. 5,173,419.

This invention was made in part with Government support under U.S.-Israel Binational Agricultural Research and Development Fund (BARD) grant number US-1723-89. The Government has certain rights in the invention.

TECHNICAL FIELD

This invention is directed to isolation of chitinases for biological control of chitin-containing fungi and insects.

BACKGROUND OF THE INVENTION

Application of broad-spectrum pesticides is the primary method used for controlling fungal and insect pests. Such application has resulted in significant environmental pollution and ecological disruption. Pesticide residues are found in food and groundwater and often eliminate beneficial organisms resulting in emergence of secondary pests. Furthermore, as the target pests become less susceptible to the pesticide, there can be a resurgence of the original pest, requiring application of excessive quantities of pesticides for control.

A number of strategies for biological or biorational control of fungal and insect pests have been envisioned. Among the more attractive strategies are those that target an attribute that is pest specific. One target that has been selected is the structural polymer chitin, which is present in insects and some fungi that attack plants, but is absent in higher plants and vertebrates. U.S. Pat. No. 4,751,081 follows this approach and is directed to novel chitinase-producing bacteria strains for use for inhibiting chitinase-sensitive plant pathogens (fungi and nematodes). The approach of U.S. Pat. No. 4,751,081 lacks flexibility.

SUMMARY OF THE INVENTION

An object of the invention herein is to provide purified chitinases which can be used per se to inhibit fungi and insects that contain chitin or can be used to provide novel chitinase-producing bacteria as in U.S. Pat. No. 4,751,081 or can be used to isolate genes coding for them which can be inserted into a genome of a plant needing protection from a chitin-containing pest.

The chitinases that are the subject of the instant invention are isolated from Trichoderma harzianum strain P1. This strain was deposited with the American Type Culture Collection, 12301 Parklawn Drive, Rockville, Md. 20852 on May 20, 1991, under the terms of the Budapest Treaty, and has been assigned accession number ATCC 74058.

The chitinases herein inhibit chitin-containing fungi and insects.

One chitinase herein is an essentially pure protein and has endochitinase activity and has a molecular weight of 36 kDa (as determined by sodium dodecyl sulfate polyacrylamide gel electrophoresis after the protein was prepared under reducing conditions, on direct comparison to migration of a 36 kDa protein) and an isoelectric point of 5.3±0.2 as determined based on its elution profile from a chromatofocusing column. It has a molecular weight of 40 kDa (as determined by sodium dodecyl sulfate polyacrylamide gel electrophoresis after the protein was prepared under reducing conditions, from a regression based on the log of the molecular weight of standard proteins) and an isoelectric point of 3.9 as determined by isoelectric focusing electrophoresis from a regression of distance versus isoelectric point of standard proteins. It has an optimum activity at about pH 4 with a gradual decline to about pH 7. This chitinase is sometimes described hereinafter as the endochitinase herein.

Another chitinase herein has exochitinase activity and has a molecular weight of 36 kDa (as determined by sodium dodecyl sulfate polyacrylamide gel electrophoresis after the protein was prepared under reducing conditions, on direct comparison to migration of 36 kDa protein) and an isoelectric point of 4.4±0.2 as determined based on its elution profile from a chromatofocusing column. It has a molecular weight of 40 kDa (as determined by sodium dodecyl sulfate polyacrylamide gel electrophoresis after the protein was prepared under reducing conditions, from a regression based on the log of the molecular weight of standard proteins) and an isoelectric point of 3.9 as determined by isoelectric focusing electrophoresis from a regression of distance versus isoelectric point of standard proteins. It has chitobiase activity, as indicated by its substrate specificity. It has an optimum activity between pH 4 and pH 7. This chitinase is purified to greater than a 75-fold increase in specific activity compared to its activity in a culture filtrate of Trichoderma harzianum strain P1 having accession No. ATCC 74058. This chitinase may be obtained as an essentially pure protein or in purified condition may be present with a minor amount, e.g., up to 40% by weight (total chitobiase basis), of a chitobiase having a molecular weight of 36 kDa (as determined by sodium dodecyl sulfate polyacrylamide gel electrophoresis after the protein was prepared under reducing condition, from regression based on the log of the molecular weight of standard proteins) and an isoelectric point of 3.9 as determined by isoelectric focusing electrophoresis from a regression of distance versus isoelectric point of standard proteins. This chitinase in the form of an essentially pure protein may be described hereinafter as the chitobiase herein.

These chitinases are sometimes referred to collectively hereinafter as the "purified chitinases herein" or as chitinases "of the invention herein".

Where the molecular weight was determined by sodium dodecyl sulfate polyacrylamide gel electrophoresis after the protein was prepared under reducing condition, from regression based on the log of the molecular weight of standard proteins, the proteins were seven standard proteins obtained from Sigma Chemical Co., having molecular weights ranging from 14.2 to 66 kDa, and molecular weights were estimated from a regression equation of the log of molecular weight of the standard proteins versus distance migrated; the seven standard proteins and their molecular weights in kDa are respectively α-lactalbumin, 14.2; soybean trypsin inhibitor, 20.1; trypsinogen, phenylmethylsulfonyl fluoride treated, 24; carbonic anhydrase, 29; glyceraldehyde-3-phosphate, 36; egg albumin, 45; and bovine albumin, 66. When the isoelectric point was determined by isoelectric focusing electrophoresis from a regression of distance versus isoelectric point of standard proteins, comparison was to 12 standard proteins obtained from Pharmacia LKB Biotechnology having isoelectric points ranging from pH 3.5 to pH 9.3; the standard proteins and their isoelectric points are respectively amyloglucosidase, 3.5; methyl red dye, 3.75; soybean trypsin inhibitor, 4.55; β-lactoglobulin, 5.2; bovine carbonic anhydrase B, 5.85; human carbonic anhydrase B, 6.55; horse myoglobin cynocytic band, 6.85; horse myoglobin basic band, 7.35; lentil lectin acidic band, 8.15; lentil lectin middle band, 8.45; lentil lectin basic band, 8.65; and trypsinogen, 9.3. In both cases a linear regression was employed and $r^2$ values ranged from 0.94 to 0.99. For determination of pH optima, 50 mM citric acid and 50 mM of either $K_2HPO_4$ (endochitinase) or $K_3PO_4$ (chitobiase) were prepared and these two solutions were mixed in various ratios to give various pH values and assays were run in triplicate for each pH value and nitrophenyl-β-D-N,N'-diacetylchitobioside and nitrophenyl-β-D-N,N',N"-triacetylchitotriose were used as substrates for chitobiase and endochitinase respectively.

A further embodiment of the invention herein involves a biologically pure (i.e., free of contaminating protein) composition containing endochitinase (enzyme that cleaves chitin randomly) and chitobiase (enzyme that cleaves dimeric units from chitin), preferably the endochitinase herein and the chitobiase herein, in a weight ratio ranging from 3:1 to 1:1.2.

The term "essentially pure" is used herein to mean the presence of a single protein band on a sodium dodecyl sulfate polyacrylamide gel submitted to electrophoresis under reducing conditions and stained with silver stain. The term "in purified condition" means "essentially pure" with exception as stated.

The term "inhibit" is used herein to mean reduce the growth and/or development of fungi or insects compared to where inhibiting agent is not present.

The term "endochitinase activity" is used herein to mean ability to cleave chitin randomly. Such activity is readily determined by an assay to measure reduction of turbidity of a suspension of purified chitin by an agent wherein reduction of turbidity indicates endochitinase activity for the agent. The method of purification of the chitin is described in Vessey, J. C., et al, *Transact. Brit. Mycol. Soc.* 60, 133–143 (1973) and involves grinding and washing crab shell chitin (Sigma Chemical Co.) with distilled water, washing with a mixture containing ethanol:diethyl ether:HCl (50:50:1), bleaching with NaOCl, dissolving in HCl precipitating by diluting with ice water, and then repeatedly washing with water adjusted to pH 8.5 until the pH of the chitin equals at least 3. The assay involves the following: One g. of purified chitin is suspended in 100 ml 50 mM $KHPO_4$ buffer pH 6.7. To a test tube is added 0.5 ml of this suspension; then 0.5 ml of the test sample is added. The tube is incubated at 30° C. for 24 hours and then diluted with 5 ml water. The optical density of a suspension is determined at 510 nm. The percentage reduction in turbidity is calculated relative to addition of a sample without enzyme.

As used herein, the term "endochitinase" refers to enzymes that randomly cleave chitin.

The term "exochitinase activity" is used herein to mean ability to cleave chitin from one end. Such activity is readily determined by standard assays by release of chromogenic p-nitrophenol from p-nitrophenyl-N-acetyl-β-D-glucosaminide or p-nitrophenyl-β-D-N,N'-diacetylchitobiose, which substrates respectively measure for activity of β-N-acetylglucosaminidase (nagase activity) and N,N'-diacetylchitobiase (chitobiase activity). The assays are the same except for the substrate and involve the following: A substrate solution is formed by dissolving 3 mg of substrate in 10 ml 50 mM $KHPO_4$ buffer pH 6.7. Fifty μl of a substrate solution is added to a well in a microtiter plate (Corning). Thirty μl of test solution is added, and incubation is carried out at 50 ° C. for 15 minutes. Then the reaction is stopped by addition of 50 μl of 0.4 M $Na_2CO_3$, and the optical density is read at 410 nm. Enzyme solutions may have to be diluted, since optical density readings should be below 1.0. Activity is calculated as the optical density X the dilution factor.

As used herein, the term "chitobiase" means enzyme that cleaves dimeric unit from chitin except when otherwise indicated. Chitobiase is sometimes described herein as "biase." As used herein the term "nagase" means enzyme that cleaves monomeric units from chitin. Both are identified using the enzyme assays described above.

A further aspect of the invention herein involves inhibiting the germination of a chitin-containing fungus which comprises contacting such fungus with an antifungal effective amount of chitinase of the invention herein or of the biologically pure composition herein containing endochitinase and chitobiase. In a preferred use, the fungus is from the genera Fusarium, Botrytis, Trichoderma (different from *Trichoderma harzianum* stain P1), Uncinula or Ustilago.

A further aspect of the invention herein involves the λgtll recombinant containing a cDNA encoding for the endochitinase herein. This λgtll recombinant was deposited with the American Type Culture Collection, 12301 Parklawn Drive, Rockville, Md. 20852 on Jul. 6, 1992, under the terms of the Budapest Treaty as Bacteriophage P1, and has been assigned accession number ATCC 55338.

A further aspect of the invention herein involves the gene encoding for the endochitinase herein removed from the DNA of said λgtll recombinant by the restriction enzyme, Not I.

DETAILED DESCRIPTION

Figure 1:
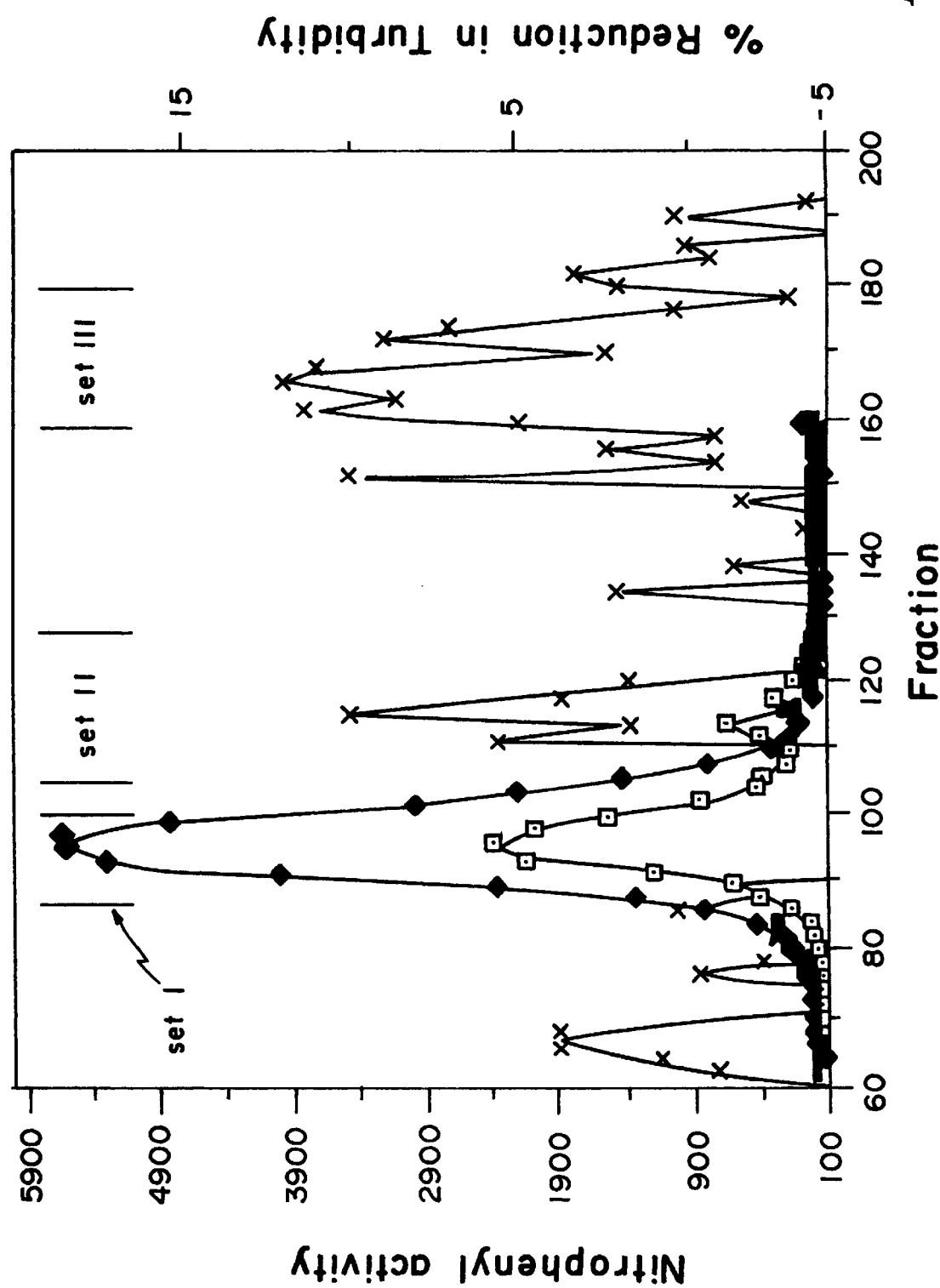
FIG. 1 depicts the elution pattern for the concentrated broth of Example I and provides a graph of endochitinase activity (Fraction vs. % Reduction in Turbidity) denoted by x's, a graph of chitobiase activity (Fraction vs. Nitrophenyl activity) denoted by open boxes, and a graph of nagase activity (Fraction vs. Nitrophenyl activity) denoted by filled-in diamonds.

*Trichoderma harzianum* strain P1 (ATCC 74058) arose as a spontaneously occurring isolate on placement of *Trichoderma harzianum* strain 107 on a medium containing 500 ppm of the fungicide iprodione by inventor A. Tronsmo. Strain 107 was isolated from wood shavings by Dr. C. Dennis in Norfolk, England and was selected by Tronsmo and Dennis as a cold tolerant isolate in a survey for biocontrol agents effective in cold climates. *Trichoderma harzianum* strain P1 (ATCC 74058) has been evaluated as a biocontrol agent as described in Tronsmo, A., *Norwegian Journal of Agricultural Sciences*, 3, 157–161, 1989 (biological control of storage rot on carrots) and has been successfully used as a biocontrol agent of *Botrytis cinerea*, a fungus affecting strawberries, grapes and apples as described in Tronsmo, A., Biological Control, 1, 59–62, 1991 and Harman, G. and Tronsmo, A., unpublished.

The purified protein chitinases herein are obtained from *Trichoderma harzianum* strain P1 (ATCC 74058) as follows: The strain is readily cultured, for example, in modified Richard's medium (composition in one liter of water of 10 g $KNO_3$, 5 g $KH_2PO_4$, 13 g $MgSO_4$, 20 mg $FeCl_3$, 10 g crab shell chitin (Sigma Chemicals), 10 g Polyclar AT (an insoluble polyvinylpyrrolidone from GAF Corp) and 150 ml V8 juice (Campbell Soup Company)) at 25° C. After 3 to 5 days of culturing, the hyphal mass is removed to provide a broth which is dialyzed to remove small molecular weight molecules and then concentrated about 30-fold. The concentrated broth is subjected to liquid chromatography to collect a fraction with chitobiase activity with low nagase activity and a fraction with only endochitinase activity. The fractions are concentrated and the proteins are eluted using a chromatofocusing column. The turbidity reducing portion of the endochitinase activity fraction elutes as a single peak as the essentially pure protein having endochitinase activity, a molecular weight of 36 kDa (as determined by sodium dodecyl sulfate polyacrylamide gel electrophoresis after the protein was prepared under reducing conditions, on direct comparison to migration of a 36 kDa protein) and an isoelectric point of 5.3±0.2 as determined based on its elution profile from a chromatofocusing column, and a molecular weight of 40 kDa (as determined by sodium dodecyl sulfate polyacrylamide gel electrophoresis after the protein was prepared under reducing conditions, from a regression based on the log of molecular weight of standard proteins) and an isoelectric point of 3.9 as determined by isoelectric focusing electrophoresis from a regression of distance versus the isoelectric point of standard proteins. For the other fraction, a chitobiase portion elutes as a single peak at pH 4.3–4.6 (variation between runs). The chitobiase portion is indicated by polyacrylamide gel electrophoresis under non-reducing conditions to contain an intensively staining protein which has chitobiase activity and has a molecular weight of 36 kDa (as determined by sodium dodecyl sulfate polyacrylamide gel electrophoresis after the protein was prepared under reducing conditions, on direct comparison to migration of a 36 kDa protein), and an isoelectric point of 4.4±0.2 as determined based on its elution profile from a chromatofocusing column, and a molecular weight of 40 kDa (as determined by sodium dodecyl sulfate polyacrylamide gel electrophoresis after the protein was prepared under reducing conditions, from a regression based on the log of the molecular weight of standard proteins), and an isoelectric point of 3.9 as determined by isoelectric focusing electrophoresis from a regression of distance versus isoelectric point of standard proteins. Chitobiase can be separated from contaminating proteins by isoelectric focusing on a Rotofor apparatus and consists of two proteins of similar isoelectric point. The larger of the two proteins (40 kDa as determined by sodium dodecyl gel electrophoresis, after the protein was prepared under reducing conditions, from a regression based on the log of the molecular weight of standard proteins), stains more intensively following sodium dodecyl sulfate-polyacrylamide gel electrophoresis and is denoted the protein of the major band. The other chitobiase is denoted the protein of the minor band. The protein of the major band can be obtained in pure form (i.e., uncontaminated by protein of the minor band), if the purification proceeds over several weeks or if the chitobiase is dried in a Speedvac vacuum dryer, presumably since the protein of the minor band is degraded over time or during drying in the Speedvac.

As indicated above, a further embodiment of the invention herein involves a biologically pure (i.e., free of contaminating protein) composition containing endochitinase (enzyme that cleaves chitin randomly) and chitobiase (enzyme that cleaves dimeric units from chitin) in a weight ratio ranging from 3:1 to 1:1.2, preferably ranging from 2:1 to 1:1. This composition provides synergistic antifungal effect compared to endochitinase or chitobiase alone and is considered to be a general occurrence, that is to be the case for all endochitinases and all chitobiases. Preferably the endochitinase is the endochitinase herein and the chitobiase is the chitobiase herein.

The purified chitinases herein, and the biologically pure compositions herein containing endochitinase and chitobiase, inhibit chitin-containing fungi and chitin-containing herbivorous insects. The chitin-containing fungi inhibited by the purified chitinases herein include, for example, species from genera including Fusarium, Gliocladium, Rhizoctonia, Trichoderma, Uncinula, Ustilago, Erysiphe, Botrytis, Saccharomyces, Sclerotium, and Alternaria. The chitin-containing herbivorous insects inhibited by the purified chitinases herein include, for example, Lepidoptera including *Trichoplusia ni* (cabbage looper), *Pieris rapae* (imported cabbage worm), corn earworm, gypsy moth, pink boll worm, tobacco bollworm, diamondback moth, codling moth and spruce budworm; Coleoptera including Colorado potato beetle, boll weevil, Mexican bean beetle and corn rootworm; Homoptera including citrus psylla, cotton aphid, peach-potato aphid and California red scale; Thysanoptera, including onion thrips; Orthoptera including migratory locusts; Hemiptera including rice stink bug; Diptera including Hessian fly and cabbage root fly; Acari including European red mite, citrus red mite and two spotted mite; Siphonoptera including Lucerne flea; Isoptera including harvester termite; and Hymenoptera including leaf cutting ants.

Inhibition of the aforementioned by the purified chitinases herein or biologically pure composition of endochitinase and chitobiase is readily carried out by contacting the fungus or insect with the chitinase or the biologically pure composition.

The purified chitinase or combinations thereof or biologically pure composition as described above can be utilized as a solution in a concentration, for example, of 50 ppm to 1000 ppm enzyme and applied in the form of a spray, or as a solid wherein the chitinase ingredient(s) is (are) present together with an agriculturally acceptable adhesive carrier, e.g., methyl cellulose or gum arabic, and applied as a powder.

Application can be, for example, to the seed, foliage or roots of a plant to be protected from a chitin-containing insect or plant-pathogenic fungus, or the soil surrounding said plant, or to a chitin-containing fungus or insect to be inhibited.

The purified chitinases herein can also be used to isolate genes coding for them. This can be carried out as follows:

Lyophillized mycelium obtained from *Trichoderma harzianum* P1 (ATCC 74058) is ground into a fine powder and suspended in a lysis buffer. The suspension is treated with oligo dT cellulose resin which absorbs mRNA, which has a polyadenylated (poly $A^+$) sequence at the 3' end. Unbound cellular debris, chromatin DNA, ribosomal RNA, membranes and other molecules are removed by washing the resin. The mRNA is eluted with a low salt buffer and recovered by ethanol precipitation. This procedure yields 20–100 μg of poly $A^+$ mRNA per gram of dried mycelium. An mRNA isolation kit is commercially available (e.g., from Invitrogen of San Diego, Calif.) for this procedure.

Oligo dT primers are added to 10 μg poly $A^+$ mRNA with the first cDNA strand synthesized by adding reverse transcriptase and dNTP's. The mRNA is degraded from the mRNA:cDNA hybrid and the second cDNA strand is synthesized by adding dNTP's, DNA polymerase 1, T4 DNA polymerase and *E. coli* ligase. Linkers are added to the newly synthesized cDNA molecules and the molecules are ligated into a viral expression vector, e.g., λgt11, to form viral particles containing a cDNA Library. Insertion of the linkered cDNA is upstream of the β-galactosidase stop codon. This formation of viral particles containing a cDNA library from the isolated poly $A^+$ mRNA is readily carried out utilizing a commercially available kit (e.g., from Invitrogen). The viral particles express the cDNA coding sequence when placed into *E. coli*.

*E. coli*, strain Y1090, is lytically infected with the viral particles. At the appropriate time, the plaque lawn plate is overlain with a coated membrane that stimulates expression of the β-galactosidase gene containing the ligated cDNA molecule. Expressed fusion particles bind to the membrane, which is probed with polyclonal antibodies specific for the chitinase of interest. Detection of those plaques expressing the genes of interest is determined using a colony screening system. Those plaques expressing the genes of interest are isolated.

The polyclonal antibodies used above are formed by injecting 25 μg of purified chitinase weekly into a rabbit, for a total of six injections. Total antibodies are isolated from the rabbit serum (Goding, J. W., Monoclonal Antibodies, Academic Press, London, 1983), with cross-reactivity and specificity determined using Western blots (Burnett, W. N., *Anal. Biochem.*, 112, 195–203 (1981).

The gene (cDNA insert) can be removed from the λgt11 recombinant by using the restriction enzyme, Not I.

The genes produced as above can be inserted into microorganisms by known methods, e.g. as in U.S. Pat. No. 4,751,081. The transgenic microorganisms can be used to produce chitinase or as biocontrol agents.

The genes produced as above can be also inserted by known methods into plants (e.g., as described in European patent application 339,009) as a defense against chitinase-sensitive pests.

The Rotofor apparatus, mentioned above and used in the examples below, is manufactured by Bio Rad and is a free solution isoelectric focusing apparatus for preparative protein purification on the basis of isoelectric point. It consists of a cylindrical horizontal focusing chamber which rotates about its axis to eliminate thermal and gravitational convection and can hold up to 58 ml of solution to be separated. The chamber contains 19 polyester membrane screens arranged in parallel within the focusing chamber. These screens allow the proteins to migrate during focusing but maintain separation patterns until the moment of harvesting. The solution containing the sample to be separated is mixed with an appropriate ampholyte solution, and the admixture is placed evenly in the horizontal apparatus. A current is applied, and the ampholytes migrate to the position where they have a net zero electrical charge, and in this way a pH gradient is formed. The proteins to be separated also migrate to the region containing the pH where they have a net zero charge (i.e., to the pH of their isoelectric point). Once this separation has occurred, separate samples are collected from each of the 20 compartments provided by the 19 polyester membrane screens by a vacuum sampling apparatus.

The invention is illustrated in the following specific examples:

EXAMPLE I

Modified Richard's medium (as described hereinbefore) containing 1% chitin from crab shells as the sole carbon source is placed in ten 250 ml Erlenmeyer flasks (100 ml/flask) and sterilization is carried out by autoclaving. Two ml of a heavy suspension of conidia (approximately $10^9$/ml) of *Trichoderma harzianum* strain P1 (ATCC 74058) were used to inoculate each flask and the resulting cultures were grown on a rotary shaker for 4 days at 25° C.

After four days of culturing, the hyphal mass was removed from the medium by centrifugation, and the supernatant (800 ml) was dialyzed against 50 mM $KHPO_4$ buffer pH 6.7 (MWCO 8,000) to remove small molecular weight molecules and then concentrated about 30-fold by applying polyethylene glycol (MW 35,000) to the outside of the dialysis tubing, to produce a concentrated broth.

Figure 2:
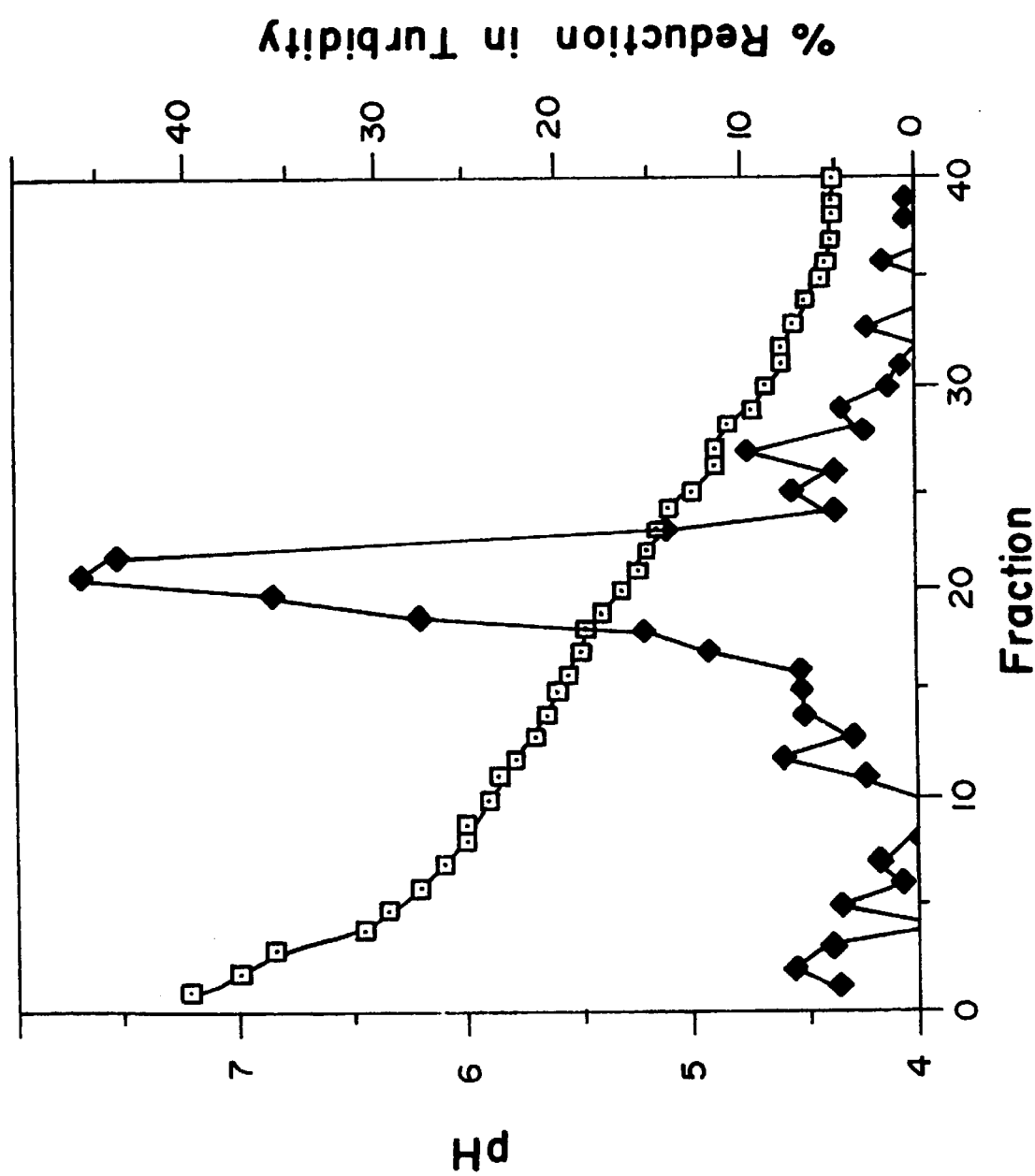
FIG. 2 depicts the elution pattern for concentrated fractions of Set III of Example I and provides a graph of endochitinase activity (Fraction vs. % Reduction in Turbidity) denoted by filled-in diamonds, and a graph of Fraction vs. pH denoted by open boxes.
Figure 3:
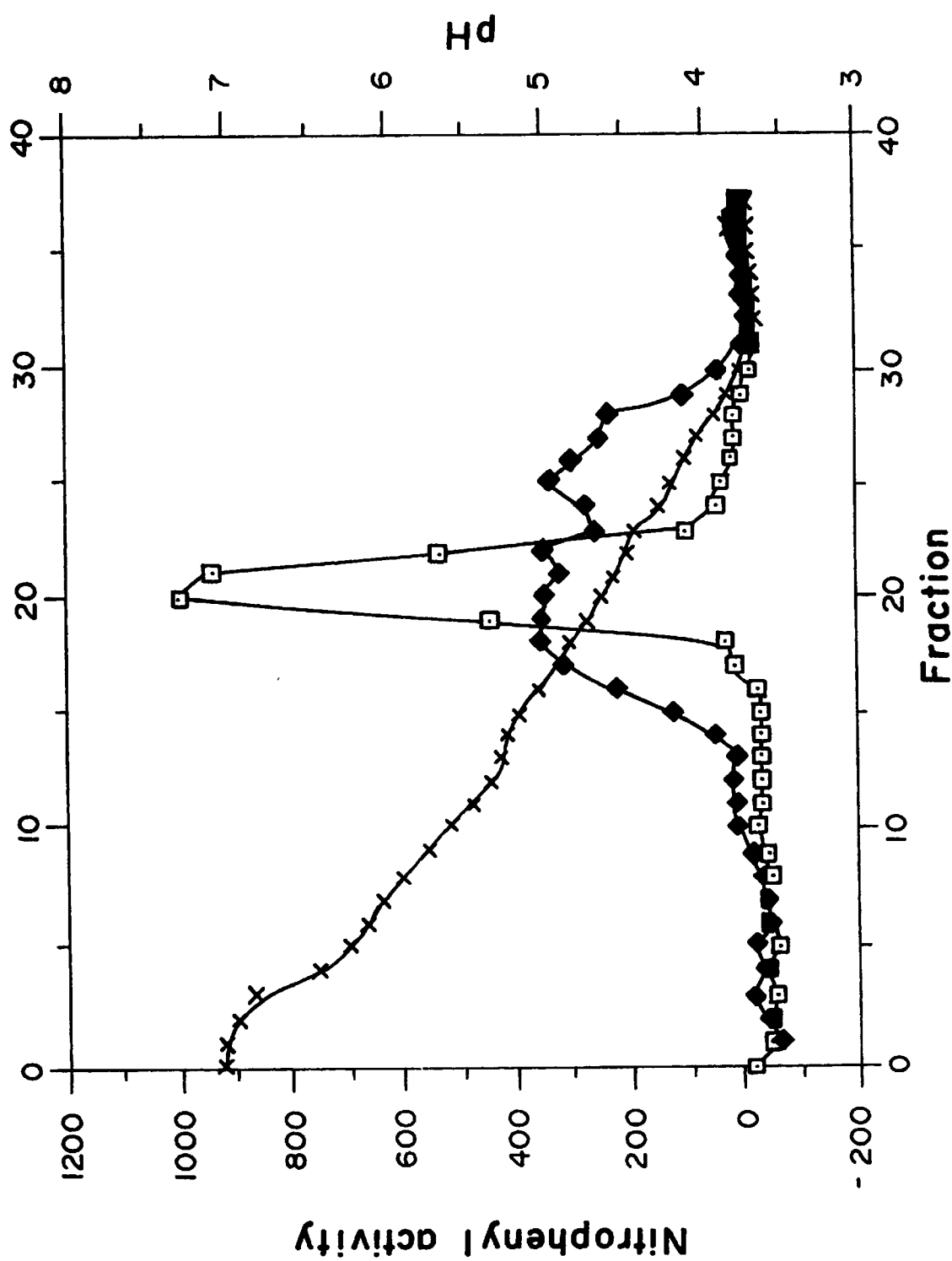
FIG. 3 depicts the elution pattern for concentrated fractions of Set II of Example I and provides a graph of nagase activity (Fraction vs. Nitrophenyl activity) denoted by filled-in diamonds, a graph of chitobiase activity (Fraction vs. Nitrophenyl activity) denoted by open boxes and a peak at fraction 20 and a graph of Fraction vs. pH denoted by x's and having a progressively descending path.

The concentrated broth (approximately 30 ml), in two separate samples, was applied to a 5×60 cm Sephacryl S-300 column and eluted with 50 mM $KHPO_4$ buffer pH 6.7 containing 200 mM NaCl. Each elution fraction consisted of about 8 ml. The elution profiles of enzyme activity are shown in FIG. 1. In FIG. 1, the X's denote the graph for % reduction in turbidity (endochitinase activity), the open boxes denote the graph for biase activity and the filled-in diamonds denote the graph for nagase activity. As shown in FIG. 1, the void volume eluted at fraction 60, and a peak of nagase and biase activity eluted at about fraction 100. At about fraction 115 there was a peak of chitobiase activity and endochitinase activity, but little nagase activity. At fractions 160–180 there was a broad peak containing only endochitinase activity. These fractions were combined into three sets, designated I, II and III, as shown on FIG. 1. Set I (approximately 120 ml) contained nagase and chitobiase activity. Set II (approximately 160 ml) contained chitobiase activity and endochitinase activity and a low level of nagase activity. Set III (approximately 200 ml) contained only endochitinase activity. Set II was combined with a similar fraction from another run on the Sephacryl column. Set III was combined with a similar fraction from another run of the Sephacryl column. The Set II combined fractions were dialyzed against 25 mM imidazole-HCl buffer 6.7 and concentrated to 20 to 60 ml. The Set III combined fractions were dialyzed against 25 mM imidazole-HCl buffer 6.7 and concentrated to 20 to 60 ml. These concentrates were applied to 1.1×25 cm chromatofocusing columns equilibrated with 25 mM imidazole buffer. The proteins were eluted with Polybuffer at a pH range of 6.7 to 4. The elution pattern for the concentrate of combined Sets III is shown in FIG. 2 wherein the open boxes denote the graph for Fraction vs. pH and the filled-in diamonds denote the graph for Fraction vs. % reduction in turbidity. The endochitinase (turbidity reducing) activity from the concentrate of combined Sets III (fraction numbers 20 to 22 consisting of approximately 24 ml) eluted at a single peak at pH 5.3±0.2. The purity of enzyme in this fraction after dialysis and drying was confirmed by polyacrylamide gel electrophoresis under non-denaturing conditions; only a single protein band was detected with silver stain. The protein in this band is determined to have a molecular weight of 36 kDa by sodium dodecyl sulfate polyacrylamide gel electrophoresis after protein was prepared under reducing conditions, on direct comparison to migration of a 36 kDa protein; a molecular weight of 40 kDa by sodium dodecyl sulfate polyacrylamide gel electrophoresis after the protein is prepared under reducing conditions, from a regression based on the log of the molecular weight of standard proteins; an isoelectric point of 5.3±0.2 based on its elution profile from a chromatofocusing column; and an isoelectric point of 3.9 by isoelectric focusing electrophoresis from a regression of distance versus isoelectric point of standard proteins. The elution pattern for the concentrate of combined Sets II is shown in FIG. 3 wherein the graph denoted by filled in diamonds is for nagase activity, the graph denoted by open boxes and a peak at about fraction 20 is for chitobiase activity, and the graph denoted by x's that progresses downwardly is for Fraction vs. pH. As shown in FIG. 3, the fractions with the greatest amount of chitobiase activity (fractions 19–22 consisting approximately of 32 ml) eluted in a single peak at about pH 4.6. In another run these fractions eluted in a single peak at about pH 4.3. As shown in FIG. 3 these fractions contained some nagase activity. This peak (after dialysis and drying) was found by polyacrylamide gel electrophoresis under non-reducing conditions to contain three protein bands. Only one of these bands, the most intensively staining one, was found to have chitobiase activity. The protein of this band was determined to have an isoelectric point of 4.4±0.2 (based on its elution profile from a chromatofocusing column), has an isoelectric point of 3.9 by isoelectric focusing electrophoresis from a regression of distance versus isoelectric point of standard proteins, was determined by sodium dodecyl sulfate polyacrylamide gel electrophoresis after the protein was prepared under reducing conditions to have a molecular weight of about 36 kDa on direct comparison to migration of a 36 kDa protein, and has a molecular weight of 40 kDa by sodium dodecyl sulfate polyacrylamide gel electrophoresis after the protein is prepared under reducing conditions and the molecular weight determined from regression based on the log of the molecular weight of standard proteins. This protein is isolated from the other two present by gel filtration liquid chromatography on Bio-Gel P-60 (Bio Rad Laboratories).

COMPARATIVE EXAMPLE I

Chitinases isolated from pea, tomato and bean were reported to be endochitinases and to have molecular weights of 27–39 kDa and isoelectric points ranging from 8.87 to 9.4.

An enzyme from *T. reesei* which is an endochitinase was estimated to have a molecular weight of 58 kDa.

The enzyme system of *Serratia marcescens* strain QMB1466 (ATCC 990) was reported to have chitobiase activity. This activity is associated, on sodium dodecyl sulfate polyacrylamide gel electrophoresis under reducing conditions, with two major protein bands of molecular weights at 52.5 and 58 kDa and two minor protein bands of molecular weights of 21.5 and 40.4 kDa. This strain is the one used in the working Example of U.S. Pat. No. 4,751,081 for chitinase activity.

EXAMPLE II

The purified endochitinase from Sets III in Example I (fraction numbers 20 to 22 of FIG. 2) and purified chitobiase enzyme from Sets II in Example I (fraction numbers 19–22 in FIG. 3), that is the fraction containing the essentially pure endochitinase having a molecular weight of 36 kDa (as determined by sodium dodecyl sulfate polyacrylamide gel electrophoresis after the protein was prepared under reducing conditions, on direct comparison to migration of a 36 kDa protein) and an isoelectric point of 5.3±0.2 based on its elution profile from a chromatofocusing column (denoted endochitinase below) and the fraction containing the protein having chitobiase activity, a molecular weight of 36 kDa (as determined by sodium dodecyl sulfate polyacrylamide gel electrophoresis after the protein was prepared under reducing conditions, on direct comparison to migration of a 36 kDa protein) and an isoelectric point of 4.4±0.2 as determined based on its elution profile from a chromatofocusing column (denoted biase below), were assayed for antifungal activity against *Fusarium sp.* and *Trichoderma harzianum* (ATCC 20847). This was carried out on the dialyzed, dried fractions, as follows: A solution containing 500 ppm of enzyme (dialyzed, dried fraction) in distilled water was prepared and was sterilized by filtration through a 0.45 $\mu$m filter. From each sterilized composition an assay mixture was prepared that contained 100 $\mu$l of the sterilized composition, 100 $\mu$l of 3× potato dextrose broth (Difco Laboratories), and 100 $\mu$l of a fungal spore suspension ($10^6$/ml). Each assay mixture was incubated. Results of spore germination after a 12 hour incubation were as follows:

TABLE 1

| Enzyme | Organism | Spore Germination % |
| --- | --- | --- |
| None (control) | *Fusarium* | 85 |
| Biase | *Fusarium* | 63 |
| Endochitinase | *Fusarium* | 58 |
| None (control) | *Trichoderma* | 49 |
| Biase | *Trichoderma* | 20 |
| Endochitinase | *Trichoderma* | 22 |

These data show that spore germination was inhibited by the enzyme solutions.

Other effects were noted as follows: Germ tube growth was inhibited after 24 hours of incubation of the Trichoderma strain by both the biase solution and the endochitinase solution. Among spores producing germ tubes, the average length (of 15 measured) for germ tubes germinating in the absence of the enzyme was 198 $\mu$m, while the average length of germ tubes in the presence of the biase was 55 $\mu$m and the average length of germ tubes in the presence of the endochitinase was 58 $\mu$m.

EXAMPLE III

Filter sterilized broth prepared from *Trichoderma harzianum* strain P1 (ATCC 74058) was compared to filter-sterilized broth from *T. virde* 105, *T. koningii* 8, *T. koningii* 417, *T. koningii* VS023, *T. harzianum* 1295-22, and *Gliocladium virens* VS031 as follows: In each case, a diet was made consisting of the following in parts by weight: 57 parts Trichoderma or Gliocladium broth, 11.4 parts wheat germ, 2 parts casein, 1.4 parts agar, 1 part Vitamin Premix (Hoffman-LaRoche #26862), 0.8 parts Wesson Salt Mixture (Bio Serv, Inc.), 0.2 parts sorbic acid, 0.1 parts methyl paraben, and 26 parts distilled water. Larvae of *T. ni* and *P. rapae* were provided with the diet, ad libitum from neonate until the controls reached the ultimate instar, and then all larvae were weighed. Only two of the fungal strains, *G. virens* VS031 and *T. harzianum* P1 (ATCC 74058), reduced the growth of both the larval *T. ni* and *P. rapae* below 60%. The filter-sterilized broth from each of these two strains was dialyzed (MWCO 8,000) to remove small molecular weight molecules and incorporated into the artificial diet as described above. Again, the broth from these two strains significantly reduced the growth of larval *T. ni* and *P. rapae*. The ammonium sulfate precipitable protein in the filter-sterilized, dialyzed broth from both strains was tested for biological activity against larval *T. ni* and *P. rapae* as above. The chitinase activity of the original P1 broth was not precipitated while that of the VS031 broth was. The ammonium sulfate precipitated protein from strain VS031 significantly reduced larval growth while that of strain P1 did not.

EXAMPLE IV

A medium containing 10 g $KNO_3$, 5 g $KH_2PO_4$, 2.5 g $MgSO_4 \times 7H_2O$, 2 mg $FeCl_3$, 10 g crab shell chitin (Sigma Chemical Co.), 150 ml of vegetable juice cocktail (V8 juice), 10 g polyvinylpyrollidone (Polyclar AT, GAF Corp.) and 1000 ml water was adjusted to pH 6 and then sterilized by autoclaving.

The medium was placed in Erlenmeyer flasks (100 ml per 250 ml flask) and each flask was inoculated with a spore suspension of *Trichoderma harzianum* strain P1 (ATCC 74058) to give about $5 \times 10^6$ conidia final concentration and the inoculated flasks were placed on a rotary shaker at 150 RPM at 25° C. for 4 or 5 days. The liquid was separated from the biomass by centrifugation at 8000×g for 10 minutes and residual particulates were removed through a glass fiber filter to provide a culture filtrate containing the enzymes of interest.

The culture filtrate was dialyzed against 50 mM $KPO_4$ buffer pH 6.7 (6 liters of buffer per liter of culture filtrate) overnight at 4° C. with stirring. After dialysis, the dialysis tubes were placed in polyethylene glycol (35,000 MW, Fluka Chemika-Biochemika) until the volume was reduced 15- to 25-fold.

The concentrated culture filtrate (approximately 15 ml) in two separate samples was applied to a 5×60 cm chromatography column packed with Sephacryl S-300 (Pharmacia LKB Biotechnology) equilibrated with 50 mM $KPO_4$ buffer pH 6.7 containing 200 mM NaCl and 0.02% $NaN_3$ and eluted with the same buffer. The concentrated culture filtrate and elution buffer were applied from the bottom of the column using a pump set to deliver 2.3 ml per minute, and fractions were collected every 5 minutes.

Figure 4:
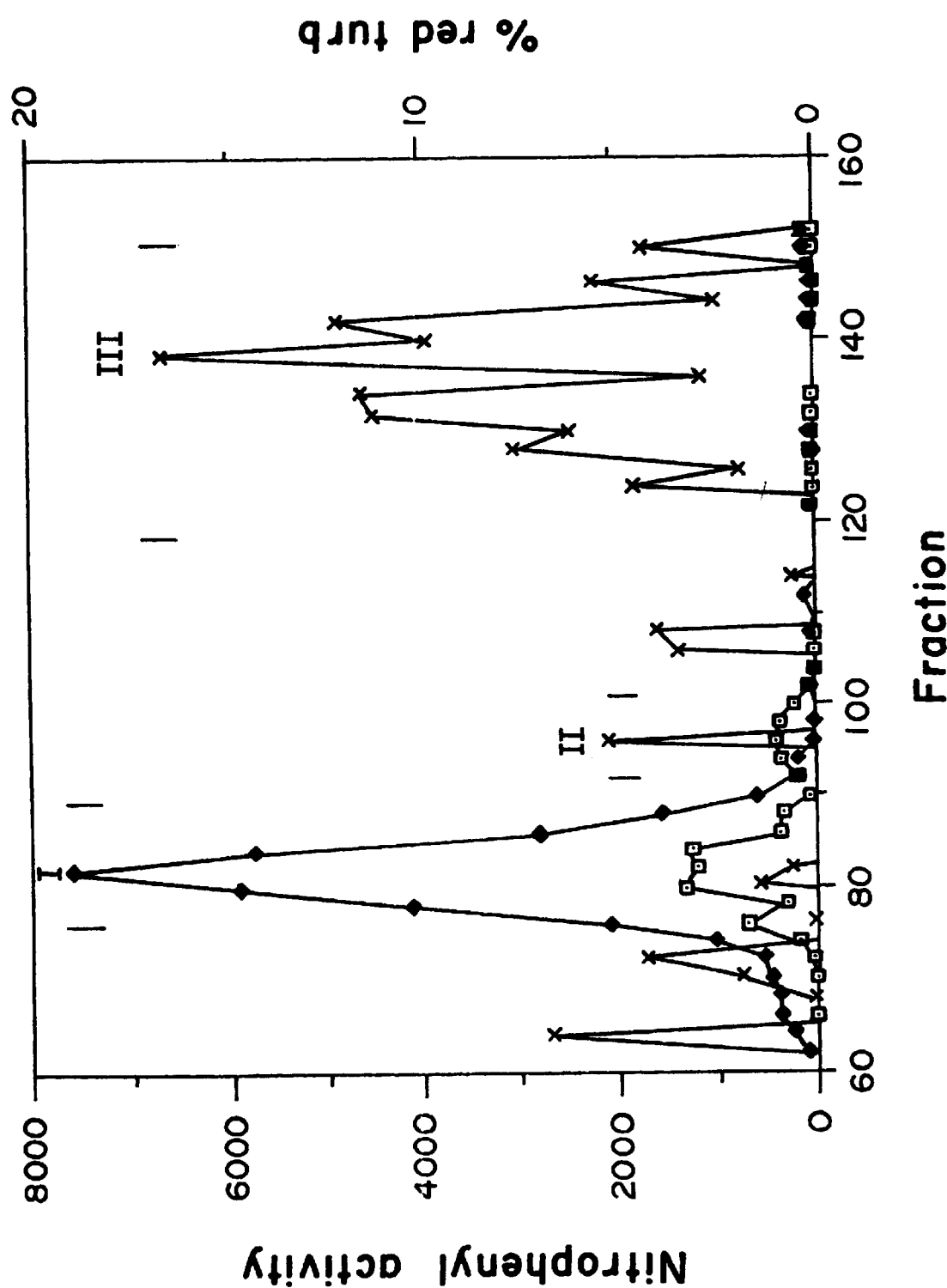
FIG. 4 depicts the elution pattern for the concentrated broth of Example IV and provides a graph of endochitinase activity (Fraction vs. % Red Turbidity, i.e., % Reduction in Turbidity) denoted by x's, a graph of chitobiase activity (Fraction vs. Nitrophenyl activity) denoted by filled in diamonds and a graph of nagase activity (Fraction vs. Nitrophenyl activity) denoted by open squares.

The elution profiles of enzyme activity are shown in FIG. 4. In FIG. 4, the x's denote endochitinase activity, the open boxes denote chitobiase activity and the filled in diamonds denote nagase activity. As shown in FIG. 4, at fractions 92–100 there was a peak of chitobiase activity together with endochitinase and nagase activity; these fractions were designated set II. As shown in FIG. 4, fractions 120–150 contained most of the endochitinase activity; these fractions were designated Set III.

Figure 5:
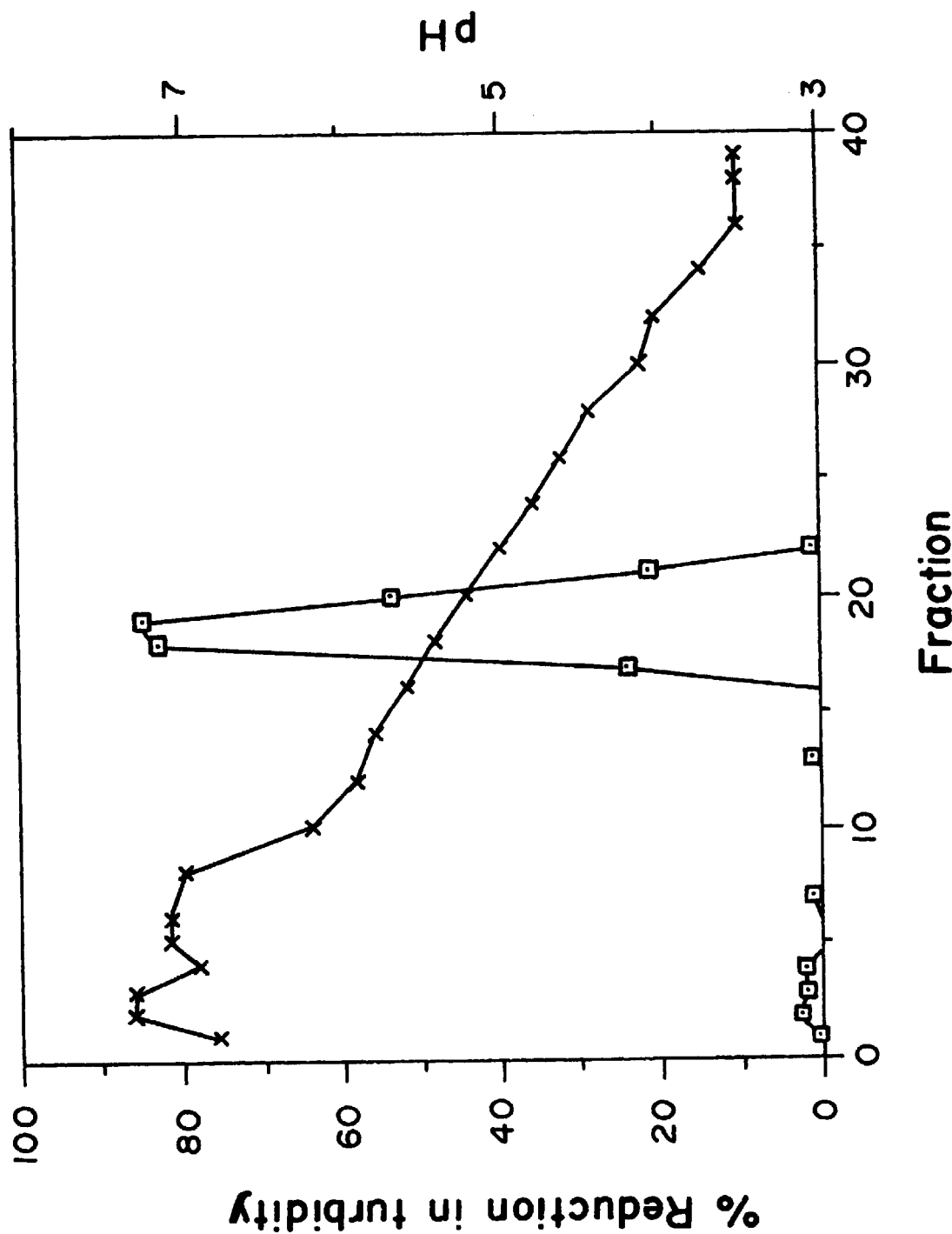
FIG. 5 depicts the elution pattern for the fractions of Set III of Example IV and provides a graph of endochitinase activity (Fraction vs. % Reduction in Turbidity) denoted by open squares, and a graph of Fraction vs. pH denoted by x's.

The fractions of Set III (345 ml) were pooled, and the combined fractions were concentrated to 25 ml in dialysis tubing immersed in polyethylene glycol (molecular weight of 35,000) overnight against approximately a 10-fold volume of 25 mM imidazole-HCl buffer pH 7. The concentrate was applied to a 1×30 cm chromatofocusing column packed with PBE 94 (Pharmacia LKB Biotechnology) equilibrated with 25 mM imidazole buffer. The proteins were eluted with Polybuffer (Pharmacia LKB Biotechnology), at a pH range of 7 to 4. The elution pattern for concentrated fractions of set III is shown in FIG. 5. In FIG. 5, the open boxes denote endochitinase activity and the x's denote pH. Electrophoresis on native, sodium dodecyl sulfate and isoelectric focusing gels showed a single protein. Activity, as determined by fluorescence of methylumbelliferyl substrate, corresponded to the protein band on isoelectric focusing and native gels and showed the protein to be an endochitinase. The molecular weight of the protein was determined to be 40 kDA (as determined by sodium dodecyl sulfate polyacrylamide gel electrophoresis after the protein was prepared under reducing conditions, from a regression based on the log of the molecular weight of standard proteins) and the isoelectric point of the protein was determined to be 3.9 by isoelectric focusing electrophoresis from a regression of distance versus isoelectric point of standard proteins. The specific activity of the purified endochitinase was determined to be 0.86 units/μg protein with the turbidity reducing assay and 2.2 nkat/μg protein when nitrophenyl-β-D-N,N',N"-triacetylchitotriose was used as the substrate. The specific activity of the endochitinase in the original culture filtrate could not be determined because said filtrate contains an inhibitor of endochitinase activity. The endochitinase was determined to have optimum activity at about pH 4 with a gradual decline to about pH 7.

Figure 6:
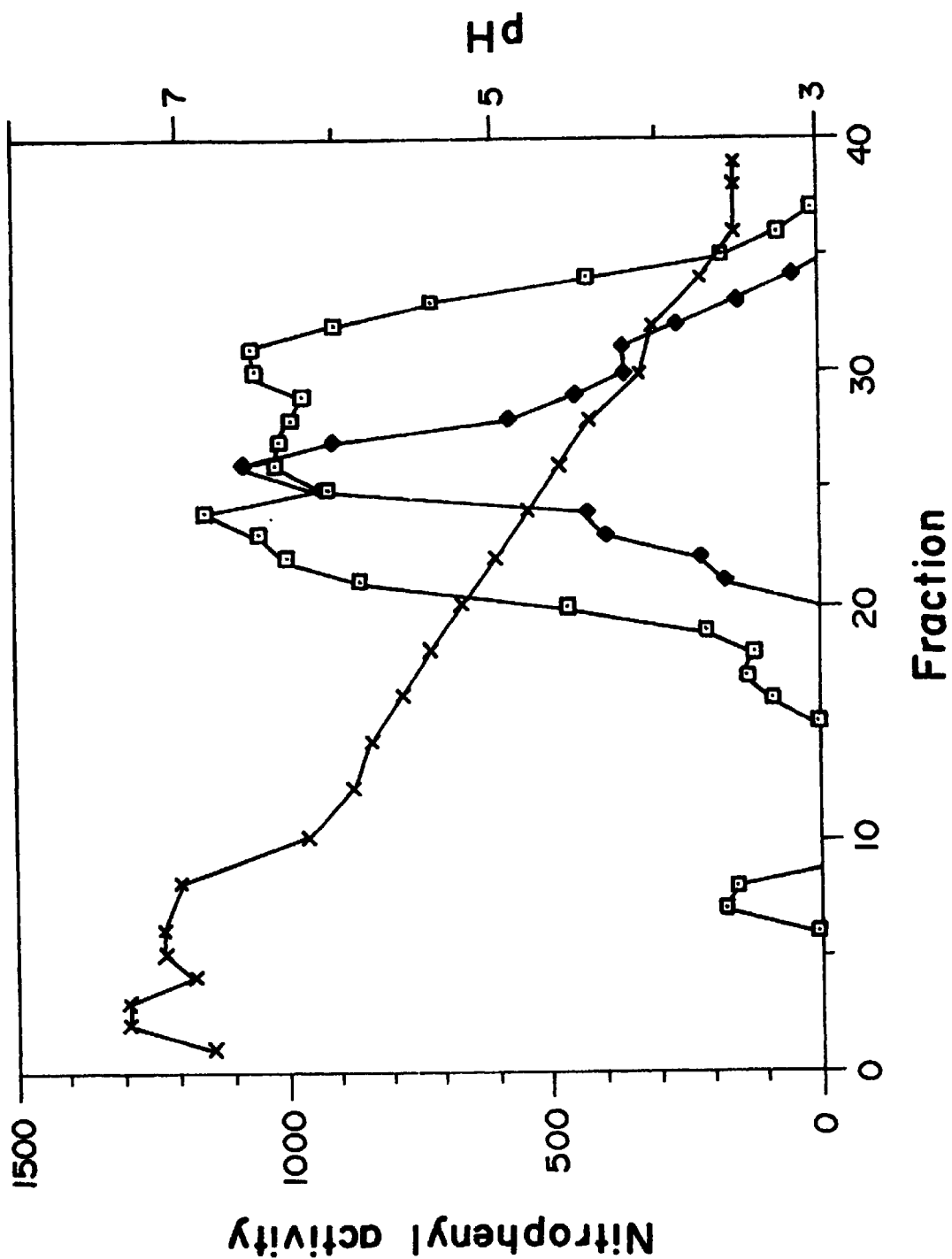
FIG. 6 depicts the elution pattern for the fractions of Set II of Example IV and provides a graph of nagase activity (Fraction vs. Nitrophenyl activity) denoted by open squares, a graph of chitobiase activity (Fraction vs. Nitrophenyl activity) denoted by filled in diamonds, and a graph of Fraction vs. pH denoted by x's.
Figure 7:
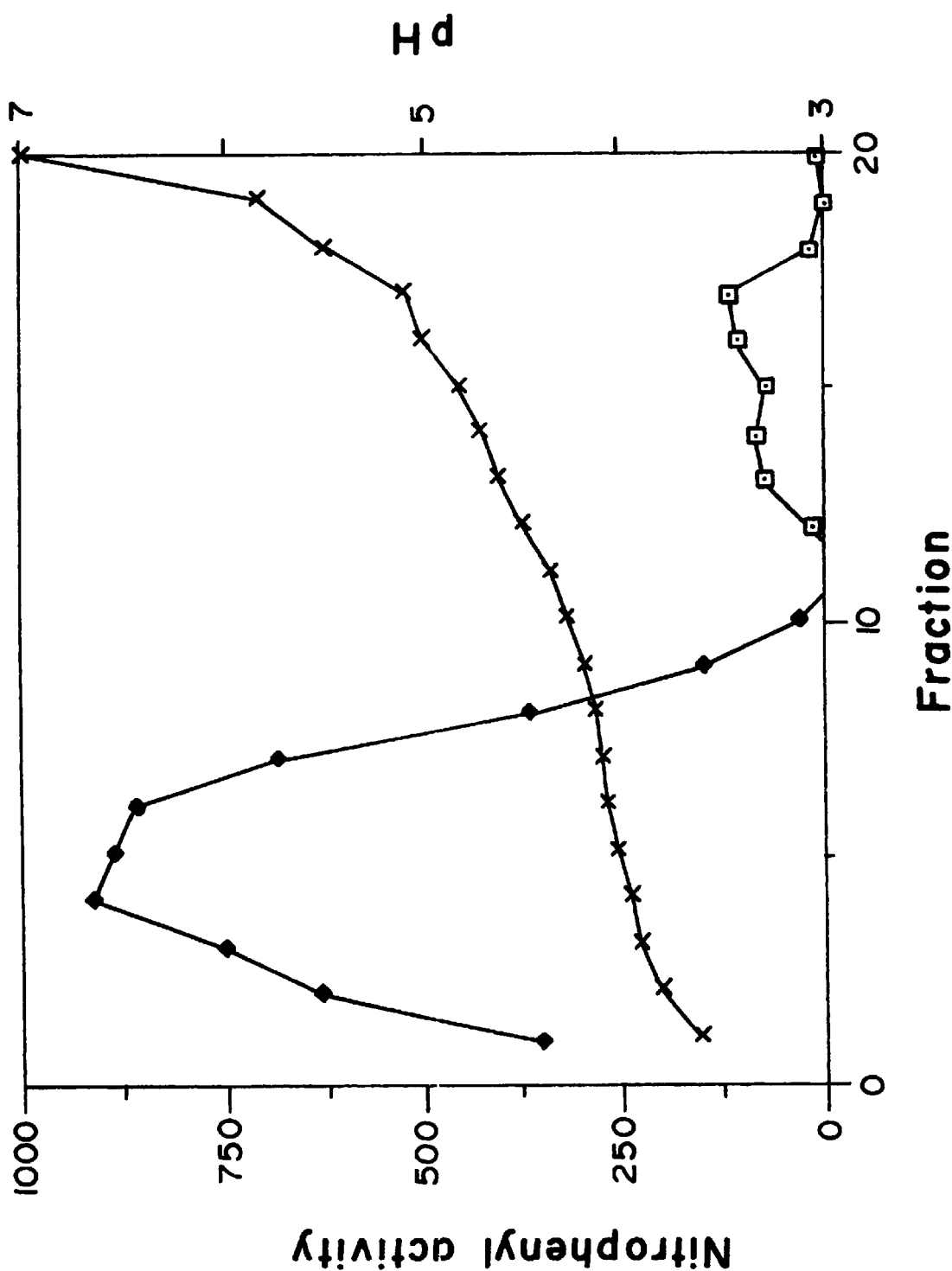
FIG. 7 depicts the elution pattern for selected fractions from chromatofocusing separation of Set II, separated according to isoelectric point on a Rotofor apparatus and provides a graph of chitobiase activity (Fraction vs. Nitrophenyl activity) denoted by filled in diamonds, a graph of nagase activity (Fraction vs. Nitrophenyl activity) denoted by open squares and a graph of Fraction vs. pH denoted by x's. The graph shown is based upon 1.5 µl of enzyme rather than the usual 30 µl since the enzyme activity was high.

The fractions of Set II (92 ml) were pooled, and the combined fractions were concentrated in dialysis tubing immersed in polyethylene glycol (molecular weight of 35000) to approximately 25 ml and then dialyzed overnight against approximately a 10-fold volume of 25 mM imidazole-HCl buffer pH 7. The concentrate was applied to a 1×30 cm chromatofocusing column packed with PBE94 (Pharmacia LKB Biotechnology) equibrated with 25 mM imidazole buffer. The proteins were eluted with Polybuffer (Pharmacia LKB Biotechnology), at a pH range of 7 to 4. The elution pattern for the concentrated fractions of set II is shown in FIG. 6. In FIG. 6, the filled in diamonds denote chitobiase activity, the open boxes denote nagase activity and the x's denote pH. In addition to chitobiase and nagase activity, a small overlapping peak of glucanase activity was detected by hydrolysis of nitrophenyl-β-D-glucopyranoside. Since the glucanase activity eluted in fractions after 28, fractions 25 to 27 were pooled for further purification. The pooled fractions were further purified by separation according to isoelectric point on a Rotofor apparatus (Bio-Rad Laboratories) employing Bio-Lyte ⅗ ampholyte at 10% v/v of the total volume and collecting peak fractions and purifying these on the Rotofor apparatus. The separation pattern for samples collected from the Rotofor apparatus is shown in FIG. 7. In FIG. 7 the filled in diamonds denote chitobiase activity, the open boxes denote nagase activity and the x's denote pH. Fractions 2 to 8 were collected and contained chitobiase activity and no endochitinase or nagase activity. The chitobiase was determined to consist of two closely spaced protein bands on sodium dodecyl sulfate, isoelectric focusing and native gels. The larger of the two bands provided a more intensively staining protein band and was the major product. These bands correspond to activity bands as determined by overlay of fluorescent enzyme-specific substrate on isoelectric focusing and native gels. The chitobiase of the major band was determined to have a molecular weight of 40 kDa (as determined by sodium dodecyl sulfate polyacrylamide gel electrophoresis after the protein was prepared under reducing conditions, from regression based on the log of the molecular weight of standard proteins) and an isoelectric point of 3.9 as determined by isoelectric focusing electrophoresis from a regression of distance versus isoelectric point of standard proteins. The chitobiase of the minor band was determined to have a molecular weight of 36 kDa (as determined by sodium dodecyl sulfate polyacrylamide gel electrophoresis after the protein was prepared under reducing conditions, from regression based on the log of the molecular weight of standard proteins) and an isoelectric point of 3.9 as determined by isoelectric focusing electrophoresis from a regression of distance versus isoelectric point of standard proteins. The chitobiase of the minor band was present at a level of no more than 40% by weight (total chitobiase basis).

In runs where the purification step was carried out over a period of several weeks or where the purified chitobiase sample was dried in a Speedvac vacuum drying apparatus, the minor band was not present and essentially pure chitobiase of the major band was obtained.

Specific activities of the chitobiase were determined at various stages of processing with the following results.

TABLE 2

| Purification step | Specific activity (nkat/mg protein) | Recovery (%) |
|---|---|---|
| Culture filtrate | 0.54 | 100 |
| After dialysis and concentration | 12.3 | 39 |
| Set II after Sephacryl chromatography | 26.2 | 29 |
| After chromatofocusing | 51.7 | 13 |
| After isoelectric focusing in the Rotofor (major band protein) | 127 | 12 |

The above results show that the activity of the chitobiase of the major band is purified more than 75 times after chromatofocusing and more than 200 times after isoelectric focusing in the Rotofor.

The chitobiase of the major band was determined to have an optimum activity between pH 4 and pH 7.

EXAMPLE V

The essentially pure endochitinase of Example IV and essentially pure chitobiase of the major band of Example IV and a 1:1 (w/w) mixture thereof were assayed for antifungal activity against *Botrytis cinerea, Fusarium solani, Ustilago avenae, Uncinula necator, Trichoderma harzianum* (ATCC 20847), *Saccharomyces cerevisiae, Fusarium graminearum, Trichoderma harzianum* strain P1 (ATCC 74058) and *Pythium ultimum* strain P4. This was carried out as follows: Equal volumes (100 μl) of fungus suspension ($10^6$ spores or cells/ml), medium and enzyme test solution of various amounts of dialyzed dried fraction in distilled water sterilized by filtration, were mixed. The medium in all cases except for *Ustilago avenae* was 3× potato dextrose broth (Difco Laboratories). In the case of *Ustilago avenae* the medium was a 3× concentration of Koller and Wubben medium, i.e., a medium containing 50 mM 2-(N-morpholino)ethanesulfonic acid containing (g/l) dipotassium hydrogen phosphate, 1.0; magnesium sulfate, 0.5; ammonium nitrate, 1.0; potassium chloride, 0.5; ferrous ammonium sulfate, 0.1; glucose, 10.0; yeast extract 1.0; and 0.5 ml of a micronutrient solution (which contained (mg/liter) sodium tetraborate decahydrate, 1500; manganese sulfate monohydrate, 15; zinc sulfate heptahydrate, 2500; cuprous sulfate pentahydrate, 100; sodium molybdate, 1000) wherein the medium was adjusted to pH 6.1 and sterilized by filtration. The assay mixtures were incubated for 22–48 hours at 20–25° C.

The results are given in the following Table 3 where "ge/re" stands for spore germination or sporidia or cell replication and "elong" stands for germ tube elongation and $ED_{50}$ means the dose for 50% inhibition of spore germination or sporidia or cell replication in the case of ge/re and 50% reduction in the length of germ tubes produced from surviving conidia as compared to length of control germ tubes (produced without enzymes present) and "n.d." stands for not determined and "chitob+endoc" stands for the 1:1 mixture of chitobiase and endochitinase.

TABLE 3

| | $ED_{50}$ for enzymes ($\mu g \times ml^{-1}$) | | | | | |
|---|---|---|---|---|---|---|
| | chitobiase | | endochitinase | | chitob + endoc | |
| FUNGI | ge/re | elong | ge/re | elong | ge/re | elong |
| *Botrytis cinerea* | 152 | 125 | 41 | 58 | 10 | 24 |
| *Fusarium solani* | 165 | 168 | 110 | 67 | 30 | 28 |
| *Ustilago avenae* | 179 | — | 135 | — | 34 | — |
| *Uncinula necator* | 180 | 173 | 35 | 30 | 13 | 10 |
| *Trichoderma harzianum* | 62 | 162 | 90 | 35 | n.d. | n.d. |
| *Saccharomyces cerevisiae* | 490 | — | 535 | — | 400 | — |
| *Fusarium graminearum* | 125 | 132 | 100 | 70 | n.d. | n.d. |
| *Trichoderma harzianum* (P1) | >1000 | >1000 | >1000 | >1000 | >1000 | >1000 |
| *Pythium ultimum* | >1000 | >1000 | >1000 | >1000 | >1000 | >1000 |

EXAMPLE VI

The synergy between the essentially pure endochitinase of Example IV and the essentially pure chitobiase of the major band of Example IV is demonstrated according to the formula in Richter, D. L., Pestic. Sci. 19:309–315, 1987. In accordance with that formula, if synergism exists $E_O(xA+$ yB)>$E_O$(x+y)A, and >$E_O$(x+y)B, where $E_O$ stands for percentage inhibition and x is the concentration of A (endochitinase herein) in the enzyme mixture and y is the concentration of B (chitobiase herein) in the enzyme mixture. In this Example, assays were carried out as in Example V except that 50 μg/ml of endochitinase was used in one case and 50 μg/ml of chitobiase was used in another case and 50 μg of a 1:1 mixture of endochitinase was used in the third case and percent inhibition was determined. Since the total enzyme concentration was the same in the three cases, synergism exists according to the formula in Richter if the percent inhibition for the mixture is greater than that for either of the individual cases.

The data obtained is set forth in Table 4 below.

TABLE 4

| Fungus | enzyme(s) (total concentration = 50 μg/ml) | | |
|---|---|---|---|
| | endochitinase ($E_o$ = % inhibition) | chitobiase ($E_o$ = % inhibition) | endochitinase + chitobiase ($E_o$ = % inhibition) |
| Botrytis cinerea | 60 | 20 | 97 |
| Fusarium solani | 20 | 12.5 | 70 |
| Uncinula necator | 72 | 12 | 93 |
| Ustilago avenae | 7.5 | 5.5 | 55 |

As indicated by the data, not only is synergism present according to the formula of Richter since the percent inhibition of the mixture is greater than the percent inhibition for the same total concentration of either of the components of the mixture but also the percent inhibition for the mixture exceeds that of the sum of the percent inhibitions for the same total concentrations of the individual components.

EXAMPLE VII

Figure 8:
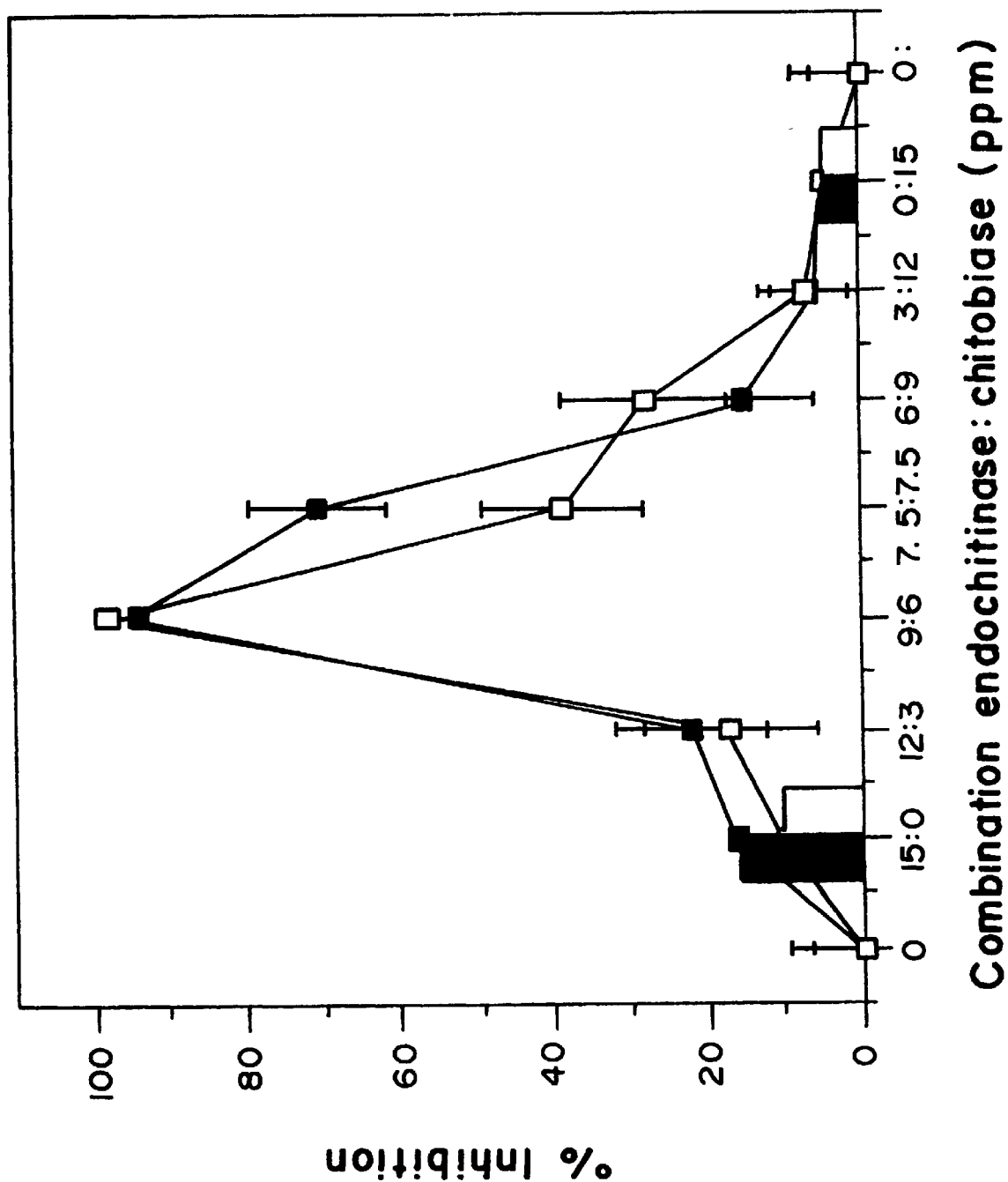
FIG. 8 depicts the synergy obtained with various combinations of endochitinase and chitobiase and shows results of Example VII.

Various combinations of the essentially pure endochitinase of Example IV and the essentially pure chitobiase of the major band of Example IV (weight ratios of 12:3, 9:6, 7.5:7.5, 6:9 and 3:12) were assayed for antifungal activity against Botrytis cinerea. Equal volumes (100 μl) of spore suspension ($10^6$/ml), 3× potato dextrose broth medium and enzyme test solution (15 ppm of enzyme combination), in distilled water, sterilized by filtration, were mixed. The assay mixtures were incubated at 25° C. for 4 hours. The results are set forth in FIG. 8 where the graph delineated by filled in blocks relates to % inhibition of spore germination and the graph delineated by open blocks relates to percent inhibition of hyphal elongation. In FIG. 8 the data at 15:0 and 0:15 is represented by bars where the solid bars represent percent inhibition of spore germination and the open bars represent percent inhibition of hyphal elongation.

EXAMPLE VIII

The gene for the endochitinase herein was isolated as follows:

I. Isolation of Messenger Ribonucleic Acid (mRNA) Biomass of induced Trichoderma harzianum strain P1 was aseptically harvested in a sterile Buchner funnel lined with Miracloth (Calbiochem, La Jolla, Calif.) and washed with RNase-free water. The biomass was placed in a sterile disposable petri plate then quick-frozen by placing the plate in liquid nitrogen. The frozen biomass was dried by placing it in a prechilled lyophilizer and establishing a vacuum. The shelf temperature of the lyophilizer was maintained at –5° C. while the condenser temperature was set at –50° C. Approximately 1 gram of lyophilized mycelium was resuspended in 20 ml of a guanidinium solution (5 M guanidinium thiocyanate; 50 mM Tris-HCl, pH 7.5; 10 mM $Na_2$ EDTA; 5% B-mercaptoethanol, added after the aforementioned solution had been sterilely filtered and just before use) and incubated at room temperature for 10 minutes. The supernatant was removed by centrifuging at 12,000×g for 10 minutes at 12° C. N-lauroylsarcosine was added to a final concentration of 2% and the mixture was incubated at 65° C. for 2 minutes. The aqueous phase was extracted with an equal volume of phenol/chloroform/isoamyl alcohol (25:24:1), then with an equal volume of chloroform/isoamyl alcohol (24:1). Sodium acetate was added to a final concentration of 300 mM and the RNA precipitated by the addition of 2.5 volumes of cold ethanol. mRNA was purified by direct affinity absorption to oligo dT cellulose resin using the FastTrack mRNA Isolation Kit (Invitrogen; San Diego, Calif.). This procedure yielded about 15 μg of poly $A^+$ mRNA.

II. Insertion of Cloned 2'-Deoxyribonucleic Acid (cDNA) into a Bacteriophage Expression Vector, λgtII About 5 μg of poly $A^+$ mRNA was used for first strand cDNA synthesis using an oligo dT primer and reverse transcriptase. The mRNA-cDNA hybrid was converted into double-stranded cDNA by the addition of RNase H, DNA polymerase I and E. coli DNA ligase. The newly formed double-stranded cDNA molecules was blunt-ended with T4 DNA polymerase and EcoR I (Not I) adaptors were added using T4 DNA ligase. Overhang ends of the adaptors were phosphorylated with T4 polynucleotide kinase. The adapted cDNAs were selected by electroelution from agarose to provide molecules ranging in size from 900 base-pairs (bp) to 7,000 bp, then ligated into lambda vector arms that had been EcoR I cut and dephosphorylated. The viral vector was encapsulated in a protein coat with approximately 60% of the vector containing a foreign insert in a total of $1.3 \times 10^5$ viral particles.

III. Production of Polyclonal Antibodies Specific for Endochitinase from T. harzianum, Strain P1

Two, eight week old female Flemish giant/Chinchilla rabbits were subcutaneously injected each week, with about 25 μg of pure endochitinase per injection, for a total of six weeks. Total immunoglobulins (Ig), containing polyclonals specific for the endochitinase, were recovered from rabbit serum by precipitation following addition of ammonium sulfate (50% of saturation) of the rabbit serum. Specificity for endochitinase was determined using ELISA and Western blotting. The two screening techniques demonstrated that the antibody that was specific for pure endochitinase was IgG. An E. coli lysate, at a 1:10 dilution, was added to the IgG solution and the mixture was incubated overnight at 4° C. and diluted 1:400 before being used to screen the cDNA library of T. harzianum strain P1.

IV. Screening the cDNA Library

A culture of E. coli, strain Y1090, was mixed with the phage particles which resulted in lytic infection, poured into a plate and incubated until viral plaques developed. The plate was overlain with a nitrocellulose membrane, that had been soaked in a solution of isopropyl-β-D-thiogalactopyranoside (IPTG) and allowed to air dry. The membrane position on the plate was marked, then carefully removed and blocked with 1% bovine serum albumin in TBS (20 mM Tris-HCl, pH 7.4: 150 mM NaCl). The membrane was probed with the polyclonal antibody solution, then washed (3×) in TBS containing 0.05% Tween-20 (TBST). Plaques expressing fusion proteins with affinity for the polyclonal antibodies were detected by hybridization to a goat antirabbit IgG (1:5000 dilution in TBS of the monovalent immunoglobulin that has a conjugated alkaline phosphatase enzyme). The membrane was washed (3×) in TBST, then developed in an alkaline phosphatase buffer (100 mM Tris, pH 9.5, 100 mM NaCl, 50 mM MgCl$_2$ containing 225 μg 4-nitro blue tetrazolium chloride and 150 μg 5-bromo-4-chloro-3-indolyl-phosphate per ml of buffer). Those viral plaques expressing the protein of interest were further purified, then stored.

V. Assaying for enzymatically active fusion protein

Enzyme assays were performed with fusion proteins, produced by the purified plaques to see if they were active. Lysogens were formed in E. coli, Y1089, with active fusion protein observed in polyacrylamide gels overlain with 4-methylumbelliferyl β-D-N,N',N"-triacetylchitotriose.

VI. Isolation of Bacteriophage Particles

Bacteriophage particles with affinity for the polyclonal antibody were isolated from lytically infected E. coli strain Y1090. Lytically infected bacterial cells were plated on LB agar and after plaques developed, about 6 ml of SM medium (50 mM Tris-HCl pH 7.5, 100 mM NaCl, 10 mM MgSO$_4$, 0.01% gelatin) was added to the plate, which was placed on a rotary shaker at 4° C. After an overnight incubation, the liquid was removed and chloroform (7% final concentration) was mixed into the liquid, with the upper aqueous phase removed by centrifugation. DNase and RNase (final concentration of 1 μg/ml of each enzyme) were added and the mixture shaken at 37° C. for 1 hr. Chloroform (7%) was again added, the mixture was centrifuged, and the aqueous phase containing the phage particles recovered. The phage particles were ready for storage in 1% chloroform or for isolation of DNA. The phage particles constitute λgtll recombinant containing a cDNA encoding for the endochitinase herein and a sample in TE buffer (100 mM Tris-HCl, pH 7.6, +1 mM EDTA) was deposited with the American Type Culture Collection, 12301 Parklawn Drive, Rockville, Md. 20852, on Jul. 6, 1992, under the terms of the Budapest Treaty and has been assigned accession number ATCC 55338.

VII. Isolation of Viral DNA

NaCl was added to suspension of bacteriophage particles to give a 1 M solution and incubated 1 hr in an ice bath. The mixture was centrifuged at 11,000×g for 10 min at 4° C. to remove cellular debris, and the supernatant recovered. Polyethylene glycol (MW 8000) was added to give a final concentration of 10% (w/v), and the mixture placed in an ice bath for 1 hr. The bacteriophage particles were recovered by centrifugation at 11,000×g for 10 min at 4° C., and the supernatant removed and discarded. The bacteriophage particles were resuspended in SM medium, an equal volume of chloroform was added, mixed, centrifuged and the aqueous phase retained. The bacteriophage particles were recovered by centrifugation at 25,000×g for 2 hr at 4° C. SM medium (1 to 2 ml) was added and the mixture was incubated at 4° C. with shaking. Proteinase K (50 μg/ml) and sodium dodecyl sulfate (final concentration 0.5% from a 20% stock solution) were added and mixed by inverting the mixture several times in a closed tube. The mixture was incubated at 50° C. for 1 hr, cooled to room temperature and an equal volume of buffer-equilibrated phenol was added. The tube was inverted several times to mix, the phases were separated by centrifugation and the upper phase recovered by gentle suction with a wide-bore pipet. The aqueous phase was extracted with an equal volume of phenol/chloroform/isoamyl alcohol (25:24:1), then with an equal volume of chloroform/isoamyl alcohol (24:1). Sodium acetate was added to a final concentration of 300 mM and the DNA precipitated by the addition of 2.5 volumes of cold ethanol.

VIII. Removal of the cDNA Insert

The foreign DNA was recovered from the DNA purified from λgtll by digestion with Not I. Only adaptors on either side of the cDNA were cut, with the gene coding for endochitinase released in an undigested state. The active sequence was 1150 bp in length.

As indicated above, the term "chitobiase" is used herein to mean enzyme that cleaves dimeric unit from chitin. Others use this term to refer to an enzyme that cleaves chitobiose (the dimer) to monomeric units. So that there can be no confusion in the minds of those reading the term herein without having referred to the definition herein, the term "chitin 1,4-β-chitobiosidase" or the term "chitobiosidase" can be used in place of the term "chitobiase" herein to mean enzyme that cleaves dimeric unit from chitin.

Variations in the invention will be obvious to those skilled in the art. Therefore, the invention is defined by the claims.

What is claimed is:

1. A biologically pure chitin-containing-fungus-inhibiting composition containing (a) endochitinase which is coded for by a gene in the genome of a fungus and (b) protein which causes release of chromogenic p-nitrophenol from p-nitrophenyl-β-D-N,N'-diacetylchitobiose but not from p-nitrophenyl-N-acetyl-β-D-glucosaminide and which is coded for by a gene in the genome of a fungus, in a weight ratio of (a):(b) ranging from 3:1 to 1:1.2.

2. The composition of claim 1 containing said endochitinase (a) and said protein (b) in a weight ratio of (a):(b) ranging from 2:1 to 1:1.

3. A biologically pure chitin-containing-fungus-inhibiting composition containing (a) endochitinase which is essentially pure chitin-containing-fungus-inhibiting protein having endochitinase activity, which is coded for by a gene in the genome of Trichoderma harzianum strain P1 having accession No. ATCC 74058 and which has a molecular weight of 40 kDa (as determined by sodium dodecyl sulfate polyacrylamide gel electrophoresis after the protein was purified under reducing conditions, from a regression based on the log of the molecular weight of standard proteins), and an isoelectric point of 3.9 (as determined by isoelectric focusing electrophoresis, from a regression of distance versus isoelectric point of standard proteins), and containing (b) chitin-containing-fungus-inhibiting protein which causes release of chromogenic p-nitrophenol from p-nitrophenyl-β-D-N,N'-diacetvlchitobiose but not from p-nitrophenyl-N-acetyl-β-D-glucosaminide and which is coded for by gene in the genome by Trichoderma harzianum strain P1 having accession No. ATCC 74058 and which has a molecular weight of 40 kDa (as determined by sodium dodecyl sulfate polyacrylamide gel electrophoresis after the protein was prepared under reducing conditions, from regression based on the log of the molecular weight of standard proteins), and an isoelectric point of 3.9 (as determined from isoelectric focusing electrophoresis from a regression of distance versus isoelectric point of standard proteins), and which is purified to result in an increase in specific activity compared to its specific activity in a culture filtrate from culturing the producing microorganism, wherein the weight ratio of (a) to (b) ranges from 3:1 to 1.1.2.

4. A method of inhibiting the germination or replication of a chitin-containing fungus of a genus selected from the group consisting of Botrytis, Fusarium, Saccharomyces, Trichoderma, Uncinula, and Ustilago, which comprises contacting such fungus with an antifungal effective amount of the composition of claim 1.

5. A method of inhibiting the germination or replication of a chitin-containing fungus of a genus selected from the group consisting of Botrytis, Fusarium, Saccharomyces, Trichoderma, Uncinula, and Ustilago, which comprises contacting such fungus with an antifungal effective amount of the composition of claim 3.

6. The composition of claim 1 wherein said endochitinase and said protein (b) are each coded for by a gene in the genome of a fungus of the genus Trichoderma.

7. The composition of claim 6 wherein said endochitinase and said protein (b) are each coded for by a gene in the genome of the species *Trichoderma harzianum*.

8. The biologically pure chitin-containing-fungus-inhibiting composition of claim 3, wherein the protein (b) is purified to result in greater than a 75 fold increase in specific activity compared to its specific activity in a culture filtrate from culturing the producing microorganism which is *Trichoderma harzianum* strain P1.

9. A chitin-containing-fungus-inhibiting protein which causes release of chromogenic p-nitrophenol from p-nitrophenyl-β-D-N,N'-diacetvlchitobiose but not from p-nitrophenyl-N-acetyl-β-D-glucosaminide which is coded for by a gene in the genome of *Trichoderma harzianum* strain P1 having accession No. ATCC 74058 and which has a molecular weight of 40 kDa (as determined by sodium dodecyl sulfate polyacrylamide gel electrophoresis after the protein was prepared under reducing condition, from a regression based on the log of the molecular weight of standard proteins), and an isoelectric point of 3.9 (as determined by isoelectric focusing electrophoresis from a regression of distance versus isoelectric point of standard proteins), said protein being purified to result in an increase in specific activity compared to its specific activity in a culture filtrate from culturing the producing microorganism.

10. The protein of claim 9 which is purified to result in greater than a 75-fold increase in specific activity compared to its specific activity in a culture filtrate from culturing the producing microorganism which is *Trichoderma harzianum* strain P1.

11. The protein of claim 10 which is purified to result in greater than a 200-fold increase in specific activity compared to its specific activity in a culture filtrate from the culturing of *Trichoderma harzianum* strain P1.

12. A method of inhibiting the germination or replication of a chitin-containing fungus of a genus selected from the group consisting of Botrytis, Fusarium, Saccharomyces, Trichoderma, Uncinula, and Ustilago, which comprises contacting such fungus with an antifungal effective amount of the protein of claim 9.

13. A method of inhibiting the germination or replication of a chitin-containing fungus of a genus selected from the group consisting of Botrytis, Saccharomyces, Uncinula and Ustilago, which comprises contacting said fungus with an antifungal effective amount of a purified chitin-containing-fungus-inhibiting protein having endochitinase activity, which is coded for by a gene in the genome of *Trichoderma harzianum* strain P1 having accession No. ATCC 74058 and which has a molecular weight of 40 kDa (as determined by sodium dodecyl sulfate polyacrylamide gel electrophoresis after the protein was prepared under reducing conditions, from a regression based on the log of the molecular weight of standard proteins), and an isoelectric point of 3.9 (as determined by isoelectric focusing electrophoresis from a regression of distance versus isoelectric point of standard proteins).

* * * * *